US006669875B2

(12) United States Patent
Meyertholen et al.

(10) Patent No.: US 6,669,875 B2
(45) Date of Patent: Dec. 30, 2003

(54) METHOD FOR MAKING A DENTAL MILL BLANK ASSEMBLY

(75) Inventors: Darin J. Meyertholen, Woodbury, MN (US); Robert M. Biegler, Woodbury, MN (US); Ryan B. Quast, White Bear Lake, MN (US); Dean K. Reidt, Cottage Grove, MN (US); John R. Cheney, Hugo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 142 days.

(21) Appl. No.: 09/741,249

(22) Filed: Dec. 18, 2000

(65) Prior Publication Data

US 2002/0074675 A1 Jun. 20, 2002

(51) Int. Cl.[7] .............................................. A61C 13/087
(52) U.S. Cl. ......................... 264/16; 264/138; 264/219; 264/266; 264/271.1; 264/328.1; 264/328.8; 264/494; 264/19
(58) Field of Search ........................... 264/16, 19, 219, 264/266, 221.1, 328.1, 494, 138, 328.8

(56) References Cited

U.S. PATENT DOCUMENTS

| 4,080,412 A | * | 3/1978 | Colpitts et al. ............... 264/17 |
| 4,411,626 A | | 10/1983 | Becker et al. |
| 4,478,580 A | | 10/1984 | Barrut |
| 4,503,169 A | | 3/1985 | Randklev |
| 4,575,805 A | | 3/1986 | Moermann et al. |
| 4,615,678 A | | 10/1986 | Moermann et al. |
| 4,663,720 A | | 5/1987 | Duret et al. |
| 4,742,464 A | | 5/1988 | Duret et al. |
| 4,766,704 A | | 8/1988 | Brandestini et al. |
| 4,776,704 A | | 10/1988 | Kopunek et al. |
| 4,837,732 A | | 6/1989 | Brandestini et al. |
| 4,842,454 A | | 6/1989 | Gustavsson et al. |
| 4,970,032 A | | 11/1990 | Rotsaert |
| 5,092,022 A | | 3/1992 | Duret |
| 5,135,393 A | | 8/1992 | Eidenbenz et al. |

(List continued on next page.)

FOREIGN PATENT DOCUMENTS

| DE | 196 12 699 | 7/1997 |
| EP | 0 455 854 | 11/1991 |
| EP | 634 150 | 2/1999 |
| WO | WO 00/20494 | 4/2000 |
| WO | WO 00/40206 | 7/2000 |
| WO | WO 01/13862 | 3/2001 |

OTHER PUBLICATIONS

JADA, vol. 128, Mar. 1997, A Review of All–Ceramic Restorations, p. 297–307.
Girrbach Dental–Systeme, diGident CadCam Frei–Form Wahl–Frei.
U.S. patent application Ser. No. 09/428,830, filed Oct. 28, 2000, Windisch et al.
U.S. patent application Ser. No. 09/428,937, filed Oct. 28, 2000, Zhang et al.
U.S. patent application Ser. No. 09/429,185, filed Oct. 28, 2000, Zhang et al.

Primary Examiner—Stefan Staicovici
(74) Attorney, Agent, or Firm—James D. Christoff

(57) ABSTRACT

A mill blank assembly for a dental prosthesis includes a milling section and a support section for supporting the assembly in a milling machine. In certain embodiments, the milling section is adhesively bonded to the support section by a direct chemical bond that provides enhanced resistance to unintentional detachment of the milling section from the support section during a subsequent machining operation. Optionally, the support section includes a passageway that receives a quantity of flowable dental restorative material used to make the milling section, such that the restorative material that is located in the passageway provides additional resistance when hardened to unintentional detachment of the milling section from the support section.

38 Claims, 2 Drawing Sheets

U.S. PATENT DOCUMENTS

| | | |
|---|---|---|
| 5,151,044 A | 9/1992 | Rotsaert |
| 5,160,749 A | 11/1992 | Fogarty |
| 5,224,049 A | 6/1993 | Mushabac |
| 5,342,696 A | 8/1994 | Eidenbenz et al. |
| 5,378,154 A | 1/1995 | Van Der Zel |
| 5,383,752 A | 1/1995 | Rheinberger et al. |
| 5,417,572 A | 5/1995 | Kawai et al. |
| 5,490,810 A | 2/1996 | Hahn et al. |
| 5,587,912 A | 12/1996 | Andersson et al. |
| 5,691,905 A | 11/1997 | Dehoff et al. |
| 5,788,498 A | 8/1998 | Wohlwend |
| 5,813,859 A | 9/1998 | Hajjar et al. |
| 5,880,962 A | 3/1999 | Andersson et al. |
| 5,910,273 A | 6/1999 | Thiel et al. |
| 6,345,984 B2 * | 2/2002 | Karmaker et al. ........... 433/173 |
| 6,488,503 B1 * | 12/2002 | Lichkus et al. ........... 433/202.1 |

* cited by examiner

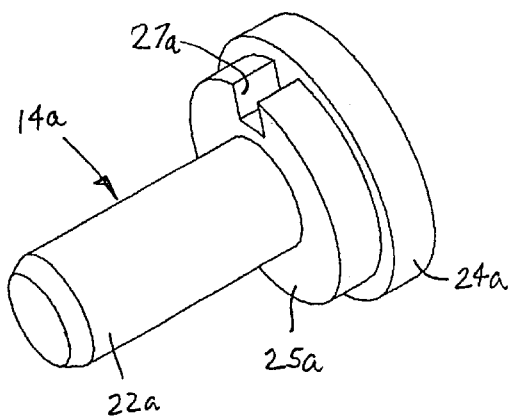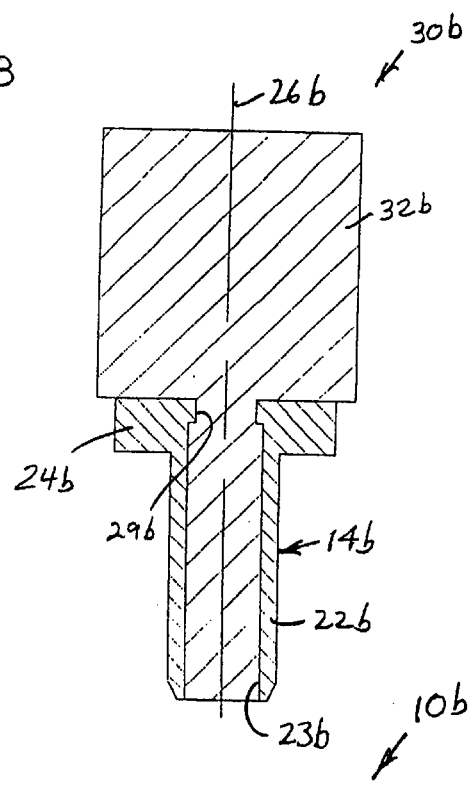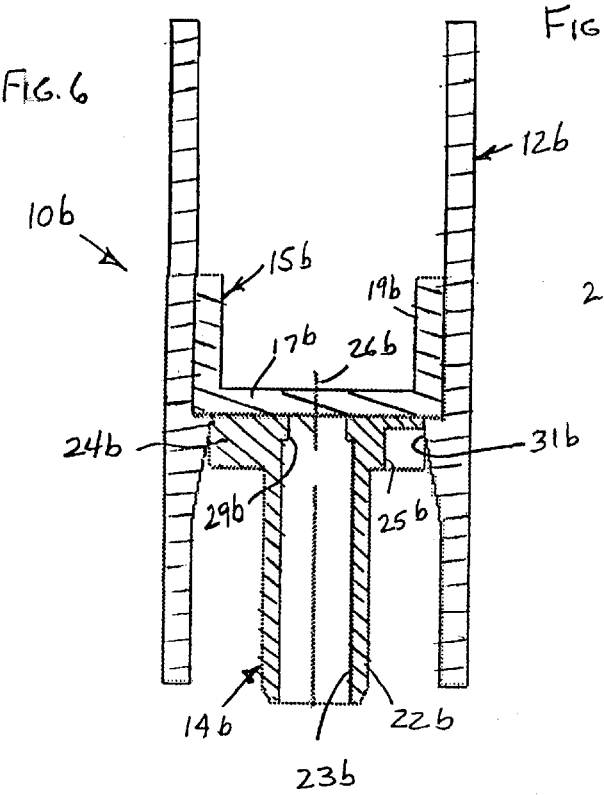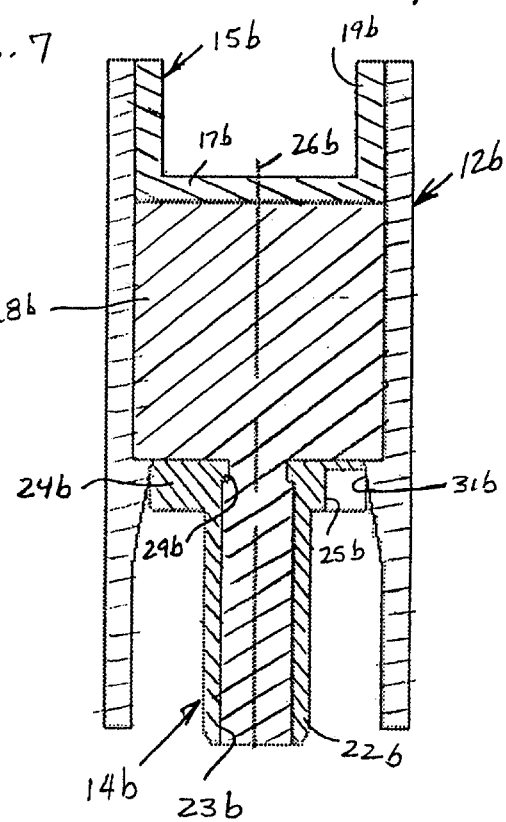

METHOD FOR MAKING A DENTAL MILL BLANK ASSEMBLY

BACKGROUND OF THE INVENTION

1. Field of the Invention

This invention broadly relates to a mill blank assembly used in the field of dentistry to create an inlay, onlay, crown, veneer, coping, bridge, bridge framework, implant, implant abutment or other restoration or restoration component. More specifically, the present invention is directed to a mill blank assembly that is especially adapted for use with computer-aided design and machining processes to create a dental prosthesis. The present invention is also directed to a method for making a dental mill blank assembly.

2. Description of the Related Art

A variety of dental procedures are known for replacing or repairing damaged, weakened or missing tooth structures. For example, a dental prosthesis commonly known as a filling is often used to fill cavities in teeth caused by tooth decay or caries. Somewhat larger prosthetics also used to fill cavities are known as inlays and onlays. Fillings, inlays and onlays may also be utilized to restore the shape of teeth that have been chipped or broken.

Other types of dental prosthetics include bridges, full crowns and partial crowns. Typically, these prosthetics are much larger than fillings and as a result are often more visible in the oral cavity. Full and partial crowns may be supported by remaining portions of the original tooth structure and/or by a post extending toward the bony region of the jaw. Bridges, on the other hand, are structures that connect to adjacent tooth structure and provide an artificial tooth or tooth crown to replace corresponding, missing structure.

In the past, fillings and some inlays and onlays were often made of a silver-colored metal alloy known as amalgam due to its relatively long life and relatively low cost. Another advantage offered by amalgam is that it allows a dental practitioner to fit and fabricate the restoration during a single session with a patient. Unfortunately, amalgam is not considered aesthetic since its silver color sharply contrasts to the appearance of natural teeth in the oral cavity.

Another material used for dental prosthetics, and particularly for larger inlays and fillings, is gold. However, like amalgam, the color of gold sharply contrasts with the appearance of natural teeth and is highly visible in the oral cavity. In addition, gold is relatively expensive in comparison to other dental materials.

As a consequence, many dental practitioners are increasingly turning to ceramic or polymer-ceramic composite materials for use to make dental prosthetics. Dental ceramic materials and dental polymer-ceramic composite materials can provide an appearance that closely matches the appearance of natural teeth. Such materials are also available in various color shades so that the practitioner can select a color that closely matches the color of adjacent tooth structure.

Dental polymer-ceramic composite materials for use as restoratives are available from various manufacturers in paste-type form. Such materials are often supplied in capsules that are releasably received in a receptacle of a hand-held dispenser. The dispenser typically includes a lever that, when depressed, extrudes a quantity of the material from the capsule and directly onto the tooth structure. The material includes a polymerization initiator that serves to harden the material once it has been placed on the tooth structure and shaped by the practitioner to resemble natural tooth structure.

A variety of techniques may be employed to help shape the unhardened restorative paste to a desired configuration once dispensed onto the patient's tooth structure. For example, if the material is used to fill a relatively small cavity, the material can be dispensed directly into the cavity and then shaped by hand. A hand instrument such as a dental pick is used to help pack the material in the cavity and to blend the external surface of the paste with adjacent, external portions of the patient's tooth. As another example, if a portion of one or more sides of a tooth is to be restored, the practitioner may elect to use a matrix band or sectional matrix band next to the tooth structure to help hold the material in place while it hardens. The matrix band or sectional matrix band serves as a formwork, similar to formwork used in concrete, to help hold the material in place and also to help define an outer surface of the composite material while it hardens.

However, larger prosthetics are often fabricated outside of the oral cavity and then placed in the patient's oral cavity once completed. For these types of prosthetics, an impression is often taken of the patient's tooth structure of interest along with adjacent regions of the gingiva, using an elastomeric impression material that provides a negative physical image of the tooth structure and gingival region. Next, a cast positive model is made by pouring a quantity of plaster of Paris into the impression and allowing the plaster of Paris to harden. The resulting plaster of Paris or "stone" model is then used in the laboratory to make a prosthetic that is ultimately transferred to the patient's oral cavity.

The laboratory procedure for making the prosthetic may be somewhat involved, depending on the type of prosthetic that is needed. In one method, for example, a wax replica of the desired crown is built on the stone model. The wax replica is then embedded in a refractory investment material and fired to create another negative physical image of the oral structure of interest. Porcelain is then forced into the investment material under pressure and heat in order to make the crown.

However, a number of disadvantages arise when the foregoing procedure is followed to make a crown. In such a procedure, the patient typically travels to the practitioner's office two times: a first time to enable an impression to be taken, and a second time a few days later after the stone model has been made and the crown has been fabricated in the dental laboratory. Moreover, if the completed crown must be returned to the laboratory because its shape, fit or appearance is not satisfactory, the patient is often then required to return to the dental office for a third visit. In many dental practices, the crown is not made in a laboratory that is part of the office but is instead sent to a central laboratory in another area of the town or region.

Furthermore, the fabrication of custom dental crowns and other prosthetics by hand from stone models is an art that involves a high degree of skill and craftsmanship, as well as intensive labor. Moreover, prosthetics that are placed in the anterior regions of the patient's oral cavity are often highly visible. It is widely considered difficult to make a porcelain prosthetic that exactly matches the translucency and color of natural teeth.

Recently, increased interest has been directed toward the use of computer automated machinery for fabricating dental prosthetics, using far less labor than prior methods such as the method for making a crown described above. For example, several systems are known for collecting a set of electronic data that is representative of the patient's tooth structure of interest. The data is then used by an automated mechanical milling machine (such as computer-aided milling machine) to fabricate a prosthetic that, when completed, closely matches the shape of natural tooth structure.

Examples of computer-aided milling machines used in the field of dentistry include the CEREC 2™ and CEREC 3™ machines available from Sirona Dental Systems of Bensheim, Germany, the DICEM™ machine from Dentronix, the VITA CELAY™ machine from Vita Zahn Fabrik of Bad Sackingen, Germany, the PRO-CAM™ machine from CadCam Ventures, of Dallas, Tex. and the PROCERA ALL CERAM™ machine from Nobel Biocare USA of Westmont, Ill. U.S. Pat. Nos. 4,837,732, 4,776,704 and 4,575,805, as well as PCT Patent Application No. WO 96/37163 also disclose systems for making dental prosthetics using computer-aided milling machines.

The fabrication of a dental prosthesis using a computer-aided machining system typically involves the use of a "mill blank", a block of material from which the prosthetic is cut. Dental mill blocks are often made of a ceramic material. Commercially available dental mill blanks include VITA CELAY™ porcelain blanks from Vita Zahn Fabrik, VITA NCERAM™ ceramic blanks from Vita Zahn Fabrik, MACOR™ micaceous ceramic blanks from Coming, and DICOR™ micaceous ceramic blanks from Dentsply. A dental mill blank made of a ceramic silica material as described in U.S. Pat. No. 4,615,678. An improved ceramic dental mill blank is described in applicant's co-pending PCT application entitled "CERAMIC DENTAL MILL BLANKS", PCT US00/19887, filed Aug. 26, 1999.

Dental mill blanks may also be made of resinous materials. An example of a dental mill blank made of a polymeric resin and a filler is described in applicant's co-pending PCT patent application entitled "DENTAL MILL BLANKS", PCT US99/10966, filed Jan. 8, 1999. Dental mill blanks made of such material exhibit superior milling characteristics such as hardness and cutting properties relative to previously known dental mill blanks.

Many commercially available dental mill blanks are made of a two-piece construction that comprises a support stub section and a milling blank section. The support section is cylindrical and adapted to fit into a collet or a Jacobs chuck of a milling machine. Often, the support section is made of metal, since the support section is ultimately detached from the milling section and does not form part of the finished prosthetic. The support section is typically made of a relatively soft metallic material such as an aluminum alloy that is easy to machine to precise tolerances.

The milling section of conventional two-piece dental mill blank assemblies is often made of one of the aesthetically-pleasing restorative materials described above so that the resulting prosthetic provides a natural appearance once placed in the oral cavity. The milling section of conventional assemblies has a flat face that is joined to a flat face of the support section by an adhesive. An example of one type of two-piece construction is described in U.S. Pat. No. 4,615,678.

It has been observed, however, that conventional dental mill blank assemblies occasionally fracture during the milling process. In some instances, the fracture occurs in the joint between the support stub section and the milling section. It is suspected that lateral forces exerted by the milling tool on the milling section create a shear force that exceeds the strength of the adhesive bond of the joint.

Unfortunately, if the milling section has broken away from the support section before the milling process has been completed, the mill blank assembly must be discarded and replaced with a new assembly. Consequently, the fracture of dental mill blank assemblies represents a time-wasting nuisance to the personnel operating the milling system and possibly to the patient. Replacement of the dental mill blank assembly with a new assembly also represents an additional cost to the dental laboratory, the dental practitioner and the patient that is best avoided if at all possible.

Applicant's previously filed patent application, U.S. Ser. No. 09/653,230 entitled "DENTAL MILL BLANK AND SUPPORT STUB ASSEMBLY", now U.S. Pat. No. 6,482,284B1, describes an improved two-piece mill blank assembly. In that assembly, a projection extends from the milling section or the support section into the remaining section and helps resist unintentional detachment of the sections from each other during a machining operation. While the inventions described in that patent application represent a significant improvement over past practice, there is a continuing need to further advance the state of the art with respect to dental mill blank assemblies.

SUMMARY OF THE INVENTION

In accordance with the invention, a dental mill blank assembly includes a milling section and a support section, and the support section is also part of a mold assembly that is used to form and make the milling section during manufacture of the assembly. In certain embodiments of the invention, the milling section is fixed to the support section by a chemical bond that begins to form within the mold cavity, such that the milling section and the support section are adhered to each other at the time that the mold assembly is opened for removal of the mill blank assembly. The use of an additional adhesive component to bond the milling section to the support section is unnecessary.

The dental mill blank assembly of the present invention is especially suitable for use in computer-aided machining systems such as the machining systems described above. The mill blank assembly presents an enhanced resistance to fracture during the time that the milling section is machined in a milling system, and safely resists forces exerted by a milling tool in lateral directions so that the dental prosthetic can be fully machined. The chemical bond between the support section and the milling section greatly reduces the likelihood that the milling section is detached from the support section during a machining operation.

In more detail, the present invention in one aspect is directed to a mill blank assembly for a dental prosthesis that comprises a milling section made of a material suitable for making a dental prosthesis. The mill blank assembly also comprises a support section having a shaft for releasably supporting the mill blank assembly in a milling machine. The support section is bonded to the milling section by a chemical bond directly between the material of the support section and the material of the milling section.

Another aspect of the invention is directed toward a dental mill blank assembly that consists essentially of a milling section and a support section. The milling section is made of a material having a composition that is different than the composition of the support section.

The present invention is also directed toward a dental mill blank assembly that includes a support section having a shaft for releasably supporting the mill blank assembly in the milling machine. The support section includes a through passageway. The mill blank assembly also includes a hardened restorative material connected to the support section. A portion of the hardened restorative material is located within the passageway. Another portion of the hardened restorative material is located externally of the passageway, serves as a milling section and is integrally connected to the portion of hardened restorative material that is located within the passageway.

Another aspect of the present invention is directed toward a method of making a dental mill blank assembly. This method includes the act of providing a mold assembly that includes a first mold component, a second mold component and a mold cavity defined at least in part by the first mold component and the second mold component. The method also includes the act of directing a quantity of restorative material into the mold cavity. The method further includes the act of reacting the restorative material with the second mold component in order to establish a chemical bond between the restorative material and the second mold component. The method also includes the act of hardening the restorative material located in the mold cavity.

Another aspect of the present invention is directed toward a method of making a dental prosthesis. The method includes the act of providing a mold assembly that includes a first mold component, a second mold component and a mold cavity defined at least in part by the first mold component and the second mold component. The method also includes the acts of directing a quantity of restorative material into the mold cavity, and establishing a bond between the restorative material and the second mold component. The method further includes the acts of hardening the restorative material located in the mold cavity, and separating the first mold component from the restorative material. The method additionally includes the acts of mounting the second mold component in a milling machine, and milling the hardened restorative material at least partially into a prosthesis.

The present invention is also directed in an additional aspect to a method of making a dental mill blank assembly. In this aspect, the method includes the act of directing a quantity of restorative material through a passageway of a support section. The method also includes the act of hardening restorative material located within the passageway as well as restorative material located externally of the passageway, such that the hardened restorative material located externally of the passageway serves as a milling section and the hardened restorative material located within the passageway resists detachment of the milling section from the support section.

Other aspects, features and advantages of the invention are described in the paragraphs that follow and are illustrated in the accompanying drawings.

BRIEF DESCRIPTION OF THE DRAWINGS

FIG. 5 is a perspective view of an alternative inner mold component for use with the mold assembly shown in FIGS. 1 and 2;

FIG. 6 is a side cross-sectional view of a mold assembly for making a dental mill blank assembly according to another embodiment of the invention, wherein the mold assembly is depicted as it might initially appear and before such time as a dental restorative material is introduced into a mold cavity of the mold assembly;

FIG. 7 is a view somewhat similar to FIG. 6 except that a dental restorative material has been introduced into the mold cavity and a plunger or third component of the mold assembly has been shifted relative to an outer component of the mold assembly; and FIG. 8 is a view somewhat similar to FIG. 7 except that the restorative material has hardened to make a milling section and the outer mold component as well as the plunger component have been removed.

DETAILED DESCRIPTION OF THE PREFERRED EMBODIMENTS

Figure 1:
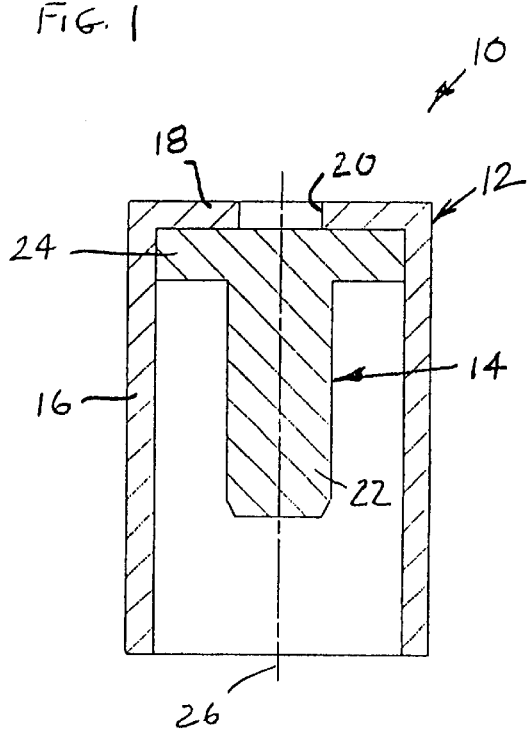
FIG. 1 is a side cross-sectional view of a mold assembly according to certain embodiments of the invention, wherein the mold assembly is shown as it initially appears and before such time as restorative material has been directed into a mold cavity of the assembly.

FIG. 1 is an illustration of a mold assembly 10 according to one embodiment of the invention. The mold assembly 10 includes an outer, hollow first mold component 12 and an inner, second mold component 14. The second mold component 14 is received in the hollow space of the first mold component 12, although other constructions are also possible.

The outer mold component 12 in this embodiment has an outer wall 16 with a generally cylindrical shape that is open at one end to admit the inner mold component 14. An opposite end of the outer mold component 12 has a flat end wall 18 with a central passageway 20 for admitting flowable dental restoration material. The end wall 18 and the outer wall 16 are integrally joined together and form a single, unitary body.

The inner mold component 14 includes a shaft 22 as well as a flange 24. Preferably, the shaft 22 and the flange 24 are integrally joined together and form a single, unitary body. Preferably, an outer end of the shaft 22 has a chamfered section for facilitating insertion of the shaft 22 in a chuck of a milling machine as will be described in the paragraphs that follow.

In the embodiment shown in the drawings, the shaft 22, the flange 24 and the outer wall 16 have circular shapes when viewed in reference planes perpendicular to a longitudinal reference axis 26. However, other shapes are also possible. For example, the cross-sectional shapes could be oval, square, rectangular, hexagonal or various other types of regular or irregular polygons, or shapes that are generally polygons but have chamfered or rounded corner portions.

To make a mill blank assembly according to one embodiment of the invention, a dental restorative material is directed through the passageway 20 and into a mold cavity of the mold assembly 10. Preferably, the restorative material is directed into the mold cavity under pressure. As the restorative material enters the mold cavity, the material bears against the front face of the flange 24 (i.e., the face of the flange 24 facing the passageway 20 in FIGS. 1–2) and an inner side of the end wall 18 and shifts the inner mold component 14 in a direction away from the passageway 20.

Figure 2:
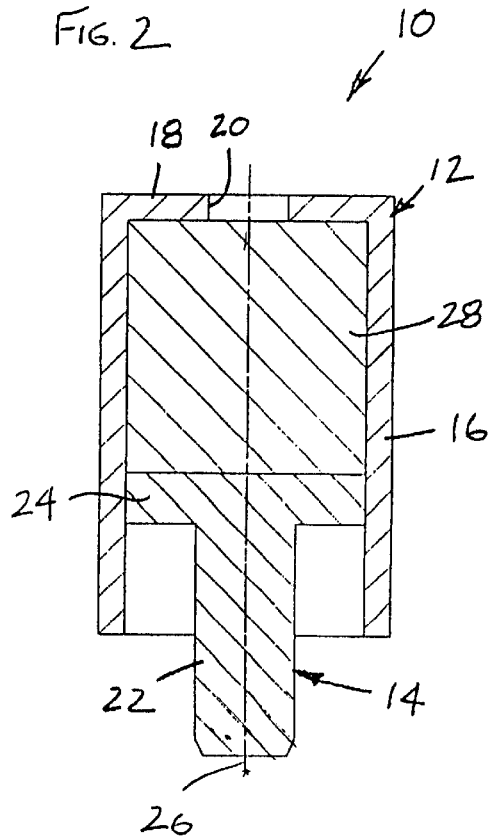
FIG. 2 is a view somewhat similar to FIG. 1 except that a quantity of restorative material has been introduced into the mold cavity and an inner mold component has shifted relative to an outer mold component in response to the introduction of the restorative material into the mold cavity.

FIG. 2 is an exemplary illustration of the mold assembly 10 as it might appear after a quantity of dental restorative material has been introduced into the mold cavity. As shown, the inner mold component 14 has moved a substantial distance away from the end wall 18, but the space between the flange 24 and the end wall 18 is occupied by the restorative material. Preferably, the cylindrical shapes of the outer edge of the flange 24 and the inner face of the outer wall 16 have nearly equal diameters and present a close mating fit so that the inner mold component 14 slides within the outer mold component 12 without undue lateral movement or "slop".

Preferably, the front face of the flange 24 is closely adjacent to the inner side of the end wall 18 before restorative material is introduced into the mold cavity. More preferably, the flange 24 is in contact with the inner side of the end wall 18 as shown in FIG. 1 before restorative material is introduced into the mold cavity. In this orientation of the components 12, 14, the volume of space in the mold cavity (ignoring the space in the passageway 20) is essentially zero.

As the mold cavity is filled, the flowing dental restorative material bears against the front face of the flange 24, thereby helping to ensure air bubbles are not created in the mass of restorative material in the mold cavity as the mold cavity enlarges in volume. Avoidance of air bubbles in the restorative material is desired so that the resulting milling section is strong and does not have voids that might otherwise appear within or on the surface of the resulting prosthetic.

Preferably, a limited amount of back pressure is applied to one or both of the components 12, 14 as the mold cavity is filled. In this manner, the likelihood of air bubbles in the resulting milling section is reduced. If, for example, the outer mold component 12 is held stationary while the mold cavity is filled, pressure is applied to the inner mold component 14 so that the inner mold component 14 does not freely move in a direction away from the passageway 20.

The back pressure can be applied by use of a piston (of a pneumatic or hydraulic piston and cylinder assembly) in contact with the end of the shaft 22. Preferably, the amount of back pressure applied to the inner mold component 14 is less than the pumping pressure. The pumping pressure is the amount of pressure that is applied to the restorative material in order to cause the restorative material to flow into the mold cavity.

In FIG. 2, the restorative material is designated by the numeral 28. FIG. 2 also shows an example of the position of the inner mold component 14 relative to the outer mold component 12 after a sufficient amount of restorative material 28 has been introduced into the mold cavity to make a milling section. The restorative material in the mold cavity is then hardened to present a unitary body that is suitable for use as a milling section.

Figure 3:
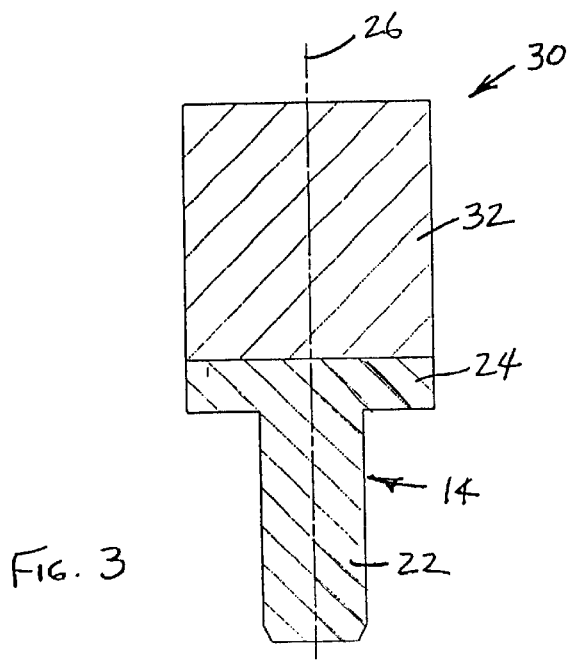
FIG. 3 is a side cross-sectional view somewhat similar to FIG. 2 except that the restorative material has been hardened to make a milling section of a mill blank assembly and the outer mold component has been removed.
Figure 4:
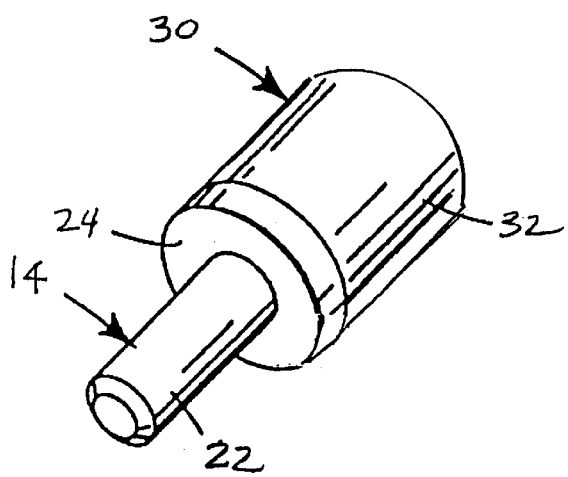
FIG. 4 is a perspective view of the mill blank assembly that is shown in FIG. 3.

FIGS. 3 and 4 are illustrations of an exemplary dental mill blank assembly 30 that can be made using the mold assembly 10. As shown, the mill blank assembly 30 includes the second mold component 14 as described above, as well as a milling section 32. In the mill blank assembly 30, the second mold component 14 serves as a support section suitable for mounting in a chuck or other coupling of a milling machine. The milling section 32 is identical to the restorative material 28 mentioned above after it has hardened.

Optionally, an outer end of the milling section 32 that is remote from the second mold component 14 is ground, sanded, machined or otherwise finished to a smooth surface. The smooth surface is not needed for subsequent machining operations during a process for making a dental prosthetic, but does improve the overall appearance of the assembly 30 as may be desired to facilitate the promotion and sale of the assembly 30 to a dental practitioner or a dental laboratory.

Finishing the end wall to a smooth surface is desired in instances where a portion of the restorative material 28 has entered the passageway 20 and hardened to leave visually apparent gate or a protrusion, especially in instances where there is a protrusion with a relatively rough outer end.

The restorative material 28 and the material of the flange 24 are selected so that a chemical bond is established between the restorative material 28 and the flange 24. Preferably, the chemical bond is provided by forces of adhesion (i.e., an interaction between molecules and/or atoms) that are established directly between the restorative material 28 and the second mold component 14 after the restorative material 28 is introduced into the mold cavity. Optionally, but not necessarily, the bond begins to form when the restorative material 28 first comes into contact with the flange 24 and before such time as the restorative material 28 begins to harden to any significant degree.

Preferably the restorative material 28 and the second mold component 14 are made of materials that establish a direct chemical bond to each other without the need for divergent chemistry. As used herein, "divergent chemistry" shall mean a composition containing effective amounts of one or more adhesive components that are not present in the restorative material 28 or the material of the second mold component 14. As an example, the use of a cyanoacrylate adhesive to adhesively bond a restorative material to an aluminum support section constitutes the use of a divergent chemistry. However, the use of a dilute solution containing methacrylate to adhesively bond or to facilitate forming an adhesive bond between a methacrylate restorative material and a polymethylmethacrylate support section does not constitute the use of divergent chemistry. The dilute solution mentioned in the last example can also be considered a primer or solvent.

A number of suitable materials are available for selection as the restorative material 28. Preferred materials for the restorative material 28 include polymerizable resins having sufficient strength, hydrolytic stability, and non-toxicity to render it suitable for use in the oral environment when hardened. Preferably, the resin is made from a material comprising a free radically curable monomer, oligomer, or polymer, or a cationically curable monomer, oligomer or polymer. Suitable resins include oxetanes, oxiranes, epoxies, methacrylates, acrylates and vinyl ethers. Alternatively, the resin may be made from a material comprising a monomer, oligomer or polymer comprising a free radically curable functionality and a cationically curable functionality.

Alternative polymers for the restorative material 28 include thermoplastic polymers, such as polycarbonates, nylon, polyetheretherketones, polyurethanes, polyimides and polyamides. The polymer material may be filled with one or more types of filler as described below.

The restorative material 28 also includes an initiator for initiating polymerization or hardening of the material. For free radical polymerization, an initiation system can be selected from systems which initiate polymerization via radiation, heat or redox/auto-cure chemical reaction. A preferred class of initiators capable of initiating polymerization of free radically active functional groups includes free radical-generating photoinitiators, optionally combined with a photosensitizer or accelerator. Such initiators are typically capable of generating free radicals for addition polymerization upon exposure to light energy having a wavelength between 200 and 800 nm. Examples of suitable free radical initiators are described in U.S. Pat. No. 5,545,676, which is expressly incorporated by reference herein.

For hardening resins comprising cationically active functional groups, an initiation system can also be selected from systems which initiate polymerization via radiation, heat, or redox/auto-cure chemical reaction. For example, epoxy polymerization may be accomplished by the use of thermal curing agents, such as anhydrides or amines.

Optionally, the initiator selected is capable of initiating both free radical and cationic polymerization. Moreover, if the resin in the restorative material is not sufficiently hardened before milling, further hardening can be carried out after milling and before use in the oral cavity.

Preferably, the restorative material 28 also includes a filler which may be either organic or inorganic in character. The filler is preferably a finely divided material that may optionally have an organic coating. Suitable coatings include silane or encapsulation in a polymeric matrix. The filler may be selected from one or more of many materials suitable for incorporation in compositions used for medical or dental applications, such as fillers currently used in dental restorative compositions and the like.

Suitable inorganic fillers include zirconia-silica, baria-silica glass, silica, quartz, colloidal-silica, fumed silica, ceramic fibers, ceramic whiskers, calcium phosphate, fluoroaluminosilicate glass and rare-earth fluorides. Suitable fillers also include nanosize heavy metal oxide particles such as described in applicant's PCT patent application entitled "RADIOPAQUE DENTAL MATERIALS WITH NANO-SIZED PARTICLES"; PCT application No. US00/04566 filed Feb. 22, 2000, which is expressly incorporated by reference herein. Other suitable fillers are described in applicant's PCT patent applications entitled "CLUSTERED PARTICLE DENTAL FILLERS" (PCT application No. US00/04614 filed Feb. 22, 2000) and "DENTAL MATERIALS WITH NANO-SIZED SILICA PARTICLES" (PCT application No. US00/05089 filed Feb. 25, 2000), both of which are expressly incorporated by reference herein. Additional suitable fillers are described in U.S. Pat. No. 4,503,169, and applicant's co-pending PCT patent application entitled "RADIOPAQUE CATIONICALLY POLYMERIZABLE COMPOSITIONS COMPRISING A RADIOPAQUE FILLER, AND METHOD FOR POLYMERIZING, SAME" (PCT No. WO 00/20494), both of which are incorporated by reference herein. The fillers may be in any morphology, including spheres, platelets, whiskers, needles, fibers, ovoids, etc. or any combination of the foregoing.

An example of a suitable restorative material 28 is "Z100" brand dental restorative from 3M Company. Further information regarding preferred restorative materials, including details of suitable compositions and method of manufacturing those materials, are set out in applicant's co-pending PCT patent application entitled "DENTAL MILL BLANKS", PCT No. WO 00/40206, which is also expressly incorporated by reference herein.

A number of suitable materials are also available for the second mold component 14. If, for example, the restorative material 28 is a methacrylate restorative material, suitable materials for the second mold component 14 include acrylic copolymers and blends of acrylic copolymers, or a methacrylate-based polymer such as polymethylmethacrylate ("PMMA"). The combination of the methacrylate restorative material 28 and the PMMA mold component 14 establishes a strong chemical bond as the restorative material 28 is hardened, such that the resulting milling section 32 is securely fixed to the second mold component 14. However, other materials for the restorative material 28 and the second mold component 14 could be selected as well so long as the two materials ultimately react to form a strong chemical bond directly to each other. Additionally, the front face of the flange 24 may be primed or softened.

Optionally, the front face of the flange 24 may include one or more projections or recesses that extend in a direction along the axis 26 or in a direction inclined relative to the axis 26. Such projections and recesses provide additional surface area for the interface between the flange 24 and the restorative material 28 and consequently enhance the strength of the chemical bond between the flange 24 and the resulting milling section 32. The projections and/or recesses also tend to establish a mechanical bond between the second mold component 14 and the resulting milling section 32, to further reduce the likelihood that the milling section 32 will become detached from the mold component 14 during a subsequent machining operation. If the mechanical bond is sufficiently strong, the chemical bond described above is unnecessary and the second mold component 14 may be made of a material that does not establish a strong chemical bond with the restorative material 28. Examples of such other materials include metals (e.g., aluminum) and other types of polymers (such as nylon, polycarbonate, polyethylene and polypropylene and ABS).

If the flange 24 includes recesses, the recesses could optionally include holes that extend completely through the flange 24. In that instance, the restorative material 28 that flows through the holes may form enlarged heads (similar to rivet heads) next to the rear face of the flange 24. These heads, when hardened, securely connect the flange 24 to the resulting milling section. Preferably, structure is provided (such as an additional flange behind the flange 24) to prevent excessive loss of restorative material 28 flowing through the holes.

The optional projection or projections of the flange 24 may be in the form of fibers, a machined surface, a mesh surface, a roughened surface or an irregular surface (for example, such as may be presented by upstanding shards of material affixed to the front face of the flange 24). Furthermore, the projection(s) could have a longitudinal axis that extends perpendicular to the reference axis 26, such as one or more projections in the shape of crossbars that extend across all or a portion of the diameter of the flange 24.

Moreover, the projections and/or recesses may present undercut areas for additionally enhancing the bond strength between the resulting milling section 32 and the second mold component 14. For example, the recesses may be beveled. As another example, the flange 24 may have a series of upstanding pegs with outermost mushroom-shaped heads that present undercut areas beneath the heads. Such mushroom-shaped heads may be manufactured by moving a heated platen against outer ends of pegs that have been formed during an injection molding process. The pegs (and preferably the entire second mold component 14) in this example are made of a heat-softenable plastic material.

When the restorative material 28 is made of a photocurable material such as one of the photocurable materials set out above, the outer wall 16 of the first mold component 12 is preferably made of a material that transmits actinic radiation. Preferably, the first mold component 12 is a unitary body that is made of a clear or translucent material that does not significantly hinder passage of actinic radiation. In addition, the first mold component 12 is preferably made of a material that does not react with the restorative material 28 and form a bond. An example of a suitable material for the first mold component 12 is poly(ethylene terephthalate) ("PET") or poly(ethylene glycol-cocyclohexane-1,4-dimethanol terephthalate) ("PETG"), although other materials may be used as well.

The restorative material 28 is cured and hardened within the mold cavity to a degree sufficient to retain its shape and remain affixed to the second mold component 14 when the first mold component 12 is removed. When the restorative material 28 is made of one of the photocurable materials mentioned above, the mold assembly 10 along with the restorative material 28 as illustrated in FIG. 2 may be placed within a dental light curing chamber in order to harden the restorative material 28. Optionally, the mold assembly 10 along with a number of additional mold assemblies may be placed on a single moving carrier or turntable that rotates or in individual, respective holders that rotate during operation of the light curing chamber in order to facilitate hardening of the restorative material 28 in a uniform manner. As an additional option, the curing chamber may include a multiple number of light sources that are arranged in a row along interior walls of the curing chamber.

The resulting milling section 32 of the mill blank assembly 30 is suitable for fabricating a wide variety of restorations, including inlays, onlays, crowns, veneers, bridges, implant abutments, copings and bridge frameworks. Various means of machining the milling section 32 may be employed to create a custom-fit dental prosthesis having a desired shape. Preferably, the prosthesis is milled by computer-aided milling equipment, such as machines sold under the trade names CEREC 2™ or CEREC 3™ from Sirona, DECIM™ from Dentronix, PRO-CAM™ from Cad-Cam Ventures or any of the other milling machines mentioned above.

By using a CAD-CAM milling device, the prosthesis can be fabricated efficiently and with precision. During milling, the contact area between the milling tool and the milling section 32 may be dry, or it may be flushed with or immersed in a lubricant. Alternatively, the contact area may be flushed with an air or gas stream. Suitable liquid lubricants are well known and include water, oils, glycerin, ethylene glycose and silicones. After milling, some degree of finishing, polishing and/or adjustment may be necessary to obtain a custom fit into the oral cavity and/or present a desired aesthetic appearance.

Optionally, the outer, cylindrical edge of the flange 24 presents a calibration surface that is located a precise distance, within very precise dimensional tolerances, from the central reference axis 26. An example of a suitable dimensional tolerance is plus or minus 0.2 mm., although somewhat smaller tolerances may be preferred. The optional calibration surface provides a reference for a milling machine. For example, the milling machine can touch a milling tool against the calibration surface before the milling process begins. In this example, the milling machine can establish a home position that accurately accounts for a current certain tool dimension (such as the length) of the milling tool and/or compensate for one or more irregularities in the shape of the mill blank assembly 30.

FIG. 5 is a perspective view of an alternative second mold component 14a according to another embodiment of the invention. Although not shown in the drawings, the second mold component 14a is part of a mill blank assembly that also includes a milling section identical to or similar to the milling section 32 described above.

The second mold component 14a is essentially the same as the second mold component 14 illustrated in FIGS. 1–4, except that the second mold component 14a includes a circular shoulder portion 25a that is located between a cylindrical flange 24a and a shaft 22a. The shoulder portion 25a has an overall diameter that is somewhat smaller than the overall diameter of the flange 24a.

Additionally, the shoulder portion 25a includes a notch 27a for receiving an indexing pin of a milling machine. As shown in the drawings, the notch 27a extends along a cylindrical edge of the shoulder portion 25a as well as along a flat end section of the shoulder portion 25a that faces the shaft 22a. The notch 27a in this embodiment has a somewhat rectangular configuration, although other shapes are also possible.

A front side of the notch 27a is closed by the flange 24a. As a result, restorative material does not flow into and through the notch 27a during filling of the mold cavity.

Other embodiments of the invention are illustrated in FIGS. 6–8. In FIG. 6, a mold assembly 10b is depicted and includes an outer, first mold component 12b. An inner, second mold component 14b is received in the hollow first mold component 12b. The mold assembly 10b also includes an inner, third mold component 15b that is also received in the first mold component 12b.

The second mold component 14b includes a shaft 22b as well as a flange 24b that is integrally connected to the shaft 22b. An elongated passageway 23b extends through the shaft 22b as well as through the flange 24b. In the illustrated embodiment, the shaft 22b, the passageway 23b and the flange 24b are symmetrically arranged about a longitudinal axis 26b, although other configurations are also possible.

The flange 24b includes an inner, circular lip 29b that extends around the passageway 23b in a location adjacent to the front face of the flange 24b. The lip 29b presents an undercut area, the advantage of which will be explained below. Preferably, the flange 24b is securely connected to an inner shoulder of the first mold component 12b so that relative movement between the second mold component 14b and the first mold component 12b does not occur during filling of the mold cavity. The secure connection between the flange 24b and the first mold component 12b may be provided by any suitable means, such as by an interference fit. In the illustrated embodiment, the inner surface of the outer wall of the first mold component 12b includes a tapered surface 31b in the vicinity of the position of the flange 24b as shown in FIGS. 6–7, and the tapered surface 31b presents a slight interference fit to help retain the first mold component 12b stationary during filling of the mold cavity.

The third mold component 15b is movable within the hollow interior of the first mold component 12b. The third mold component 15b includes an end wall 17b as well as a hollow, cylindrical outer wall 19b that is integrally joined to the end wall 17b. Preferably, the diameter of the outer wall 19b is just slightly smaller than the inner diameter of the first mold component 12b, so that the third mold component 15b is smoothly slidable within the first mold component 12b without undue lateral movement or slop. The third mold component 15b as well as the first mold component 12b are preferably made of the same materials described above in connection with the first mold component 12.

FIG. 6 is a view for exemplary purposes that shows an example of an initial position of the third mold component 15b within the first mold component 12b before restorative material is introduced into the mold cavity. Preferably, and as shown in FIG. 6, the end wall 17b in that orientation is in flat, face-to-face contact with the face of the flange 24b. In this position of the third mold component 15b, the volume of the mold cavity (ignoring the passageway 23b) is essentially zero.

Flowable restorative material is introduced into the mold cavity through the passageway 23b that extends through the second mold component 14b. Once the restorative material enters the mold cavity, the third mold component 15b and the second mold component 14b move relatively away from each other in a direction along the reference axis 26b. In this embodiment, the first mold component 12b and the second mold component 14b are held in a stationary position as the third mold component 15b shifts away from the second mold component 14b during filling of the mold cavity. As an alternative, however, it is possible to construct a mold assembly (and associated filling equipment) so that a third mold component 15b is held stationary while the remaining components move away in an opposite direction.

During a filling operation, the first mold component 12b is secured in a stationary position and a filling tube is inserted in the lower end opening of the passageway 23b when the components are oriented as depicted in FIG. 6. The filling tube (not shown) includes a gasket that preferably mates with the chamfered lower section of the shaft 22b to provide a seal. Although the gasket presses against the shaft 22b in an upwardly direction during a filling operation with sufficient pressure to compress the gasket and prevent leakage of the flowing restorative material, the tapered surface 31b of the outer wall of the first mold component 12b contacts the flange 24b in order to retain the second mold component 14b in place and in a stationary orientation.

As the mold cavity is filled, the flowing restorative material bears against an inner side of the end wall 17b, thereby helping to ensure that air bubbles are not created in the mass of restorative material in the mold cavity as the mold cavity enlarges in volume. Preferably, back pressure is applied to the third mold component 15b as the mold cavity is filled. The back pressure may be applied in a manner similar to the application of back pressure described in connection with the mold assembly 10 set out above.

FIG. 7 is an illustration of an example of the orientation of the mold components 12b, 14b, 15b after a sufficient quantity of restorative material 28b has been introduced into the mold cavity. However, a smaller or larger quantity of restorative material 28b may be directed to the mold cavity if desired.

Optionally, the flange 24b includes a notch 25b that is similar in shape to the notch 27a described above. The notch 25b is shown only in FIGS. 6 and 7 and is omitted in FIG. 8. The notch 25b is useful for receiving an indexing pin of a milling machine, such as an indexing pin that is located next to a chuck of an automated milling system.

Once a sufficient amount of restorative material 28b has been introduced into the mold cavity, the restorative material 28b is hardened. Preferably, the first mold component 12b, the second mold component 14b and the third mold component 15b are made of a material that transmits actinic radiation. As a result, the restorative material 28b that is located within the passageway 23b hardens at the same time that the restorative material 28b that is located in the mold cavity hardens.

The restorative material 28b and the second mold component 14b are preferably made of the materials described above in connection with the restorative material 28 and the second mold component 14 respectively. The restorative material 28b and the second mold component 14b chemically react with each other to form a strong adhesive bond. Once the restorative material 28b has sufficiently hardened, the first mold component 12b and the third mold component 15b are disengaged from the restorative material 28b in order to present a mill blank assembly 30b that is shown alone in FIG. 8.

Optionally, the mill blank assembly 30b can be released from the first and third mold components 12b, 15b by holding the first component 12b stationary while pushing against the second component 14b in an upwardly direction (when the mold assembly 10b is oriented as shown in FIG. 7). Once a sufficient amount of upward force is directed to the second component 14b, the interference fit between the flange 24b and the tapered inner surface 31b is overcome and the contacting surfaces of the flange 24b and the tapered surface 31b compress and expand respectively in lateral directions. This deflection enables the flange 24b to move past the tapered surface 31b so that the second mold component 14b can be removed from the interior of the first mold component 12b. The third mold component 15b is made of a material that does not react with the restorative material 28b and as a result can be easily detached from the hardened restorative material 28b at any convenient time.

As illustrated in FIG. 8, the mill blank assembly 30b includes the second mold component 14b and a milling section 32b. The second mold component 14b serves as a support section for the assembly 30b. The milling section 32b is identical to the restorative material 28b after it has hardened, except that the milling section 32b does not include the hardened restorative material located in the passageway 23b.

The mill blank assembly 30b is an advantage, in that the hardened restorative material 28b within the passageway 23b is integral with the resulting hardened milling section 32b. Consequently, the hardened restorative material within the passageway 23b provides enhanced resistance to detachment of the resulting milling section 32b in a direction away from the second mold component 14b along the reference axis 26b. The restorative material 28b within the passageway 23b also helps the milling section 32b to resist lateral forces (i.e., forces imposed by a milling tool in a direction perpendicular to the reference axis 26b).

Additionally, the lip 29b further reduces the likelihood of detachment of the milling section 32b from the second mold component 14b. Once restorative material 28b in the undercut areas beneath the lip 29b has hardened, that portion of the restorative material 28b provides a mechanical bond that resists movement of the milling section 32b in a direction away from the second mold component 14b along the reference axis 26b. Moreover, the passageway 23b provides an additional surface area of interface between the restorative material 28b and the second mold component 14b where a direct, intermolecular chemical bond is established. However, in this embodiment the chemical bond may be omitted if desired such that the hardened restorative material 28b is affixed to the second mold component 14b by essentially only the mechanical bond.

Another advantage of the mill blank assembly 30b and the mold assembly 10b is that the gate for the restorative material 28b flowing into the mold cavity is near the outer end of the shaft 22b and away from the milling section 32b. As a result, the outer surface of the milling section 32b can be molded to present a smooth, visually attractive appearance and no secondary operation (such as grinding or sanding) of the milling section 32b is needed. Optionally, however, the passageway 23b could be closed at its outer end and the mold cavity filled through an opening in the third mold component 15b. Other aspects and advantages of the mold assembly 10b and the mill blank assembly 30b are similar to the assemblies 10, 30 respectively as described above.

Those skilled in the art may recognize that a number of variations and additions may be made to the currently preferred embodiments described above. Accordingly, the invention should not be deemed limited to the specific embodiments that are set out in detail in the written specification and shown in the drawings, but instead only by a fair scope of the claims that follow along with their equivalents.

What is claimed is:

1. A method of making a dental mill blank assembly comprising the acts of:
   providing a mold assembly that includes a first mold component, a second mold component and a mold cavity defined at least in part by the first mold component and the second mold component, wherein the second mold component includes a shaft for insertion in a chuck of a milling machine;
   directing a quantity of restorative material into the mold cavity;
   reacting the restorative material with the second mold component in order to establish a chemical bond between the restorative material and the second mold component; and
   hardening the restorative material located in the mold cavity.

2. A method of making a dental mill blank assembly according to claim 1 wherein the first mold component is hollow, and wherein the second mold component is received in the first mold component.

3. A method of making a dental mill blank assembly according to claim 2 wherein the second mold component is movably received in the first mold component.

4. A method of making a dental mill blank assembly according to claim 1 wherein the act of directing a quantity of restorative material into the mold cavity includes the act of moving at least a portion of the restorative material through a passageway in the second mold component.

5. A method of making a dental mill blank assembly according to claim 4 wherein the act of providing a mold assembly includes the act of providing a third mold component that is received in the first mold component.

6. A method of making a dental mill blank assembly according to claim 5 wherein the act of directing a quantity of restorative material into the mold cavity includes the act of relatively moving the third mold component and the second mold component.

7. A method of making a dental mill blank assembly according to claim 6 wherein the second mold component and the first mold component do not move relative to each other as the third mold component and to the second mold component relatively move.

8. A method of making a dental mill blank assembly according to claim 1 wherein the act of providing a mold assembly includes the act of providing a passageway into the mold cavity through at least one of the first mold component and the second mold component.

9. A method of making a dental mill blank assembly according to claim 1 wherein the act of reacting the restorative material with the second mold component is carried out at least in part during the act of hardening the restorative material.

10. A method of making a dental prosthesis comprising the acts of:
    providing a mold assembly that includes a first mold component, a second mold component having a shaft and, a mold cavity defined at least in part by the first mold component and the second mold component;
    directing a quantity of restorative material into the mold cavity;
    establishing a chemical bond between the restorative material and the second mold component;
    hardening the restorative material located in the mold cavity;
    separating the first mold component from the restorative material;
    mounting the second mold component in a chuck of a milling machine; and
    milling the hardened restorative material at least partially into a dental prosthesis.

11. A method of making a dental prosthesis according to claim 10 wherein the act of directing a quantity of restorative material into the mold cavity includes the act of directing a portion of the restorative material into a location in contact with the second mold component.

12. A method of making a dental prosthesis according to claim 10 wherein the first mold component is hollow and wherein the second mold component is received at least partially in the first mold component.

13. A method of making a dental prosthesis according to claim 12 wherein the first mold component includes an inner side, wherein the second mold component includes a front face in contact with the restorative material, and wherein the act of directing a quantity of restorative material into the mold cavity includes the act of introducing the restorative material into the mold cavity under pressure such that the restorative material bears against the front face of the second mold component and the inner side of the first mold component and relatively moves the front face and the inner side away from each other.

14. A method of making a dental prosthesis according to claim 12 wherein the act of hardening the restorative material includes the act of directing a source of light toward the mold cavity.

15. A method of making a dental prosthesis according to claim 14 wherein the first mold component is made of a material that transmits actinic radiation, and wherein the act of directing a source of light toward the mold cavity includes the act of directing a source of light through a wall of the first mold component.

16. A method of making a dental prosthesis according to claim 10 wherein the act of directing a quantity of restorative material into the mold cavity includes the act of moving at least a portion of the restorative material through a passageway in the second mold component.

17. A method of making a dental prosthesis according to claim 10 and including the act of applying pressure to at least one of the components during at least a portion of the time that restorative material is directed into the mold cavity in order to resist free relative movement of the mold components in directions away from each other.

18. A method of making a dental prosthesis comprising the acts of:
    providing a mold assembly that includes a first mold component, a second mold component and a mold cavity defined at least in part by the first mold component and the second mold component;
    directing a quantity of restorative material into the mold cavity, wherein the act of directing a quantity of restorative material into the mold cavity includes the act of relatively sliding the first mold component and the second mold component;
    applying pressure to at least one of the components during at least a portion of the time that restorative material is directed into the mold cavity in order to resist free relative movement of the mold components in directions away from each other;

establishing a bond between the restorative material and the second mold component;

hardening the restorative material located in the mold cavity;

separating the first mold component from the restorative material;

mounting the second mold component in a milling machine; and milling the hardened restorative material at least partially into a dental prosthesis.

19. A method of making a dental prosthesis comprising the acts of:

providing a mold assembly that includes a first mold component, a second mold component and a mold cavity defined at least in part by the first mold component and the second mold component;

directing a quantity of restorative material into the mold cavity;

establishing a bond between the restorative material and the second mold component;

hardening the restorative material located in the mold cavity;

separating the first mold component from the restorative material;

mounting the second mold component in a milling machine; and milling the hardened restorative material at least partially into a dental prosthesis, wherein the act of directing a quantity of restorative material into the mold cavity includes the act of relatively moving the first mold component and the second mold component.

20. A method of making a dental prosthesis according to claim 19 wherein the act of relatively moving the first mold component and the second mold component includes the act of relatively moving the first mold component and the second mold component in a sliding, telescoping relationship.

21. A method of making a dental prosthesis according to claim 20 wherein the act of relatively moving the first mold component and the second mold component includes the act of holding the first mold component in a stationary position while the second mold component moves.

22. A method of making a dental prosthesis according to claim 10 wherein the act of establishing a bond between the restorative material and the second mold component includes the act of establishing a chemical bond.

23. A method of making a dental prosthesis according to claim 22 wherein the act of establishing a chemical bond includes the act of reacting the restorative material with the second mold component.

24. A method of making a dental prosthesis according to claim 22 wherein the act of establishing a chemical bond is carried out at least in part during the act of hardening the restorative material.

25. A method of making a dental prosthesis according to claim 10 wherein the act of establishing a bond between the restorative material and the second mold component includes the act of establishing a mechanical bond.

26. A method of making a dental prosthesis according to claim 25 wherein the mechanical bond is established in at least one undercut area of the second mold component.

27. A method of making a dental mill blank assembly comprising the acts of:

directing a quantity of restorative material through a passageway of a support section; and hardening restorative material located within the passageway as well as restorative material located externally of the passageway, such that the hardened restorative material located externally of the passageway serves as a milling section and the hardened restorative material located within the passageway establishes a bond with the support section such as a resist detachment of the milling section from the support section.

28. A method of making a dental mill blank assembly according to claim 27 wherein the support section serves as a second mold component, and wherein the method also includes the act of providing a first mold component that is hollow to receive the support section.

29. A method of making a dental mill blank assembly according to claim 28 wherein the support section is movably received in the first mold component.

30. A method of making a dental mill blank assembly according to claim 29 and including the act of providing a third mold component that is received in the first mold component.

31. A method of making a dental mill blank assembly according to claim 30 wherein the act of directing a quantity of restorative material through a passageway of the support section includes the act of directing a quantity of restorative material into a mold cavity and the act of moving the third mold component relative to the second mold component.

32. A method of making a dental mill blank assembly according to claim 28 wherein the act of hardening restorative material includes the act of directing a source of light through the first mold component.

33. A method of making a dental mill blank assembly according to claim 27 and including the act of reacting the restorative material with the support section in order to establish a chemical bond.

34. A method of making a dental mill blank assembly according to claim 27 wherein the act of directing a quantity of restorative material through a passageway of the support section includes the act of moving a portion of the restorative material into an undercut area located in the passageway.

35. A method of making a dental mill blank assembly according to claim 27 wherein the act of hardening the restorative material includes the act of directing a source of light toward the passageway.

36. A method of making a dental mill blank assembly according to claim 1 wherein the act of providing a mold assembly includes the act of selecting a material for making the first mold component that does not react with the restorative material and form a bond.

37. A method of making a dental prosthesis according to claim 10 wherein the act of providing a mold assembly includes the act of selecting a material for making the first mold component that does not react with the restorative material and form a bond.

38. A method of making a dental prosthesis according to claim 19 wherein the act of providing a mold assembly includes the act of selecting a material for making the first mold component that does not react with the restorative material and form a bond.

* * * * *

UNITED STATES PATENT AND TRADEMARK OFFICE
CERTIFICATE OF CORRECTION

PATENT NO.    : 6,669,875 B2
DATED         : December 30, 2003
INVENTOR(S)   : Meyertholen, Darin J.

It is certified that error appears in the above-identified patent and that said Letters Patent is hereby corrected as shown below:

Column 3,
Line 24, "coming" should be -- Corning--.

Column 9,
Lines 42 and 52, delete "," preceding "SAME" and preceding "BLANKS".

Column 15,
Line 50, "and to the" should be -- and the --.

Column 18,
Line 12, "a" should be -- to --.

Signed and Sealed this

Thirtieth Day of March, 2004

JON W. DUDAS
*Acting Director of the United States Patent and Trademark Office*